US00PP20854P2

(12) United States Plant Patent
Murakami

(10) Patent No.: US PP20,854 P2
(45) Date of Patent: Mar. 16, 2010

(54) ***NIEREMBERGIA* PLANT NAMED 'INTASUNNIPABU'**

(50) Latin Name: *Nierembergia hybrida*
Varietal Denomination: Intasunnipabu

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/313,690

(22) Filed: Nov. 21, 2008

(51) Int. Cl.
*A01H 5/00* (2006.01)

(52) U.S. Cl. ..... Plt./459

(58) Field of Classification Search ..... Plt./459
See application file for complete search history.

*Primary Examiner*—June Hwu
(74) *Attorney, Agent, or Firm*—C. A. Whealy

(57) ABSTRACT

A new and distinct cultivar of *Nierembergia* plant named 'Intasunnipabu', characterized by its upright, outwardly spreading and mounding plant habit; freely branching habit; freely, continuous and early flowering habit; large light blue-colored flowers; long flowering period; and good garden performance.

1 Drawing Sheet

Botanical designation: *Nierembergia hybrida* .
Cultivar denomination: 'Intasunnipabu'.

BACKGROUND OF THE INVENTION

The present invention relates to a new and distinct cultivar of *Nierembergia,* botanically known as *Nierembergia hybrida* and hereinafter referred to by the name 'Intasunnipabu'.

The new *Nierembergia* plant is a product of a planned breeding program conducted by the Inventor in Higashiomi, Shiga, Japan. The objective of the breeding program was to create new compact and mounding *Nierembergia* cultivars with freely branching habit, early flowering habit and attractive flower coloration.

The new *Nierembergia* plant originated from a cross-pollination made by the Inventor in 2003, in Higashiomi, Shiga, Japan, of a proprietary selection of *Nierembergia hybrida* identified as code number N185, not patented, as the female, or seed, parent with a proprietary selection of *Nierembergia hybrida* identified as code number 2N33, not patented, as the male, or pollen, parent. The new *Nierembergia* was discovered and selected by the Inventor as a single flowering plant within the progeny of the stated cross-pollination in a controlled environment in Higashiomi, Shiga, Japan in October, 2005.

Asexual reproduction of the new *Nierembergia* plant by vegetative cuttings in a controlled environment in Higashiomi, Shiga, Japan since November, 2005, has shown that the unique features of this new *Nierembergia* plant are stable and reproduced true to type in successive generations.

SUMMARY OF THE INVENTION

Plants of the new *Nierembergia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Intasunnipabu'. These characteristics in combination distinguish 'Intasunnipabu' as a new and distinct cultivar of *Nierembergia:*

1. Upright, outwardly spreading and mounding plant habit.
2. Freely branching habit.
3. Freely, continuous and early flowering habit.

4. Large light blue-colored flowers.
5. Long flowering period.
6. Good garden performance.

Plants of the new *Nierembergia* differ from plants of the female parent selection in the following characteristics:

1. Plants of the new *Nierembergia* are more compact than plants of the female parent selection.
2. Plants of the new *Nierembergia* flower earlier than plants of the female parent selection.
3. Plants of the new *Nierembergia* and the female parent selection differ in flower color as plants of the female parent selection have deep blue-colored flowers.

Plants of the new *Nierembergia* differ from plants of the male parent selection in the following characteristics:

1. Leaves of plants of the new *Nierembergia* are not as pubescent as leaves of plants of the male parent selection.
2. Plants of the new *Nierembergia* flower earlier than plants of the male parent selection.
3. Plants of the new *Nierembergia* have larger flowers than plants of the male parent selection.

Plants of the new *Nierembergia* can be compared to plants of *Nierembergia hybrida* 'Sunnicobu', disclosed in U.S. Plant Pat. No. 13,934. In side-by-side comparisons conducted in Higashiomi, Shiga, Japan, plants of the new *Nierembergia* and 'Sunnicobu' differed primarily in the following characteristics:

1. Plants of the new *Nierembergia* were larger and more mounded than plants of 'Sunnicobu'.
2. Plants of the new *Nierembergia* had thicker stems than plants of 'Sunnicobu'.
3. Plants of the new *Nierembergia* had larger flowers than plants of 'Sunnicobu'.

BRIEF DESCRIPTION OF THE PHOTOGRAPHS

The accompanying colored photographs illustrate the overall appearance of the new *Nierembergia,* showing the colors as true as it is reasonably possible to obtain in colored reproductions of this type. Colors in the photographs may differ slightly from the color values cited in the detailed botanical description which accurately describe the colors of the new *Nierembergia.*

The photograph at the top of the sheet comprises a side perspective view of a typical flowering plant of 'Intasunnipabu' grown in a container.

The photograph at the bottom of the sheet is a close-up view of typical flowers, flower buds and leaves of 'Intasunnipabu'.

DETAILED BOTANICAL DESCRIPTION

The aforementioned photographs and following observations, measurements and values describe plants grown in Higashiomi, Shiga, Japan, under commercial practice during the spring in an outdoor nursery with day temperatures averaging 20° C. and night temperatures averaging 13° C. Plants had been growing for six and seven months when the photographs and description, respectively, were taken. In the following description, color references are made to The Royal Horticultural Society Colour Chart, 2001 Edition, except where general terms of ordinary dictionary significance are used.

Botanical classification: *Nierembergia hybrida* 'Intasunnipabu'.

Parentage:

*Female, or seed, parent.*—Proprietary selection of *Nierembergia hybrida* identified as code number N185, not patented.

*Male, or pollen, parent.*—Proprietary selection of *Nierembergia hybrida* identified as code number 2N33, not patented.

Propagation:

*Type.*—By vegetative cuttings.

*Time to initiate roots.*—About two weeks at 20° C. to 25° C.

*Time to produce a rooted young plant roots.*—About five weeks at 20° C. to 25° C.

*Root description.*—Fibrous; white in color.

*Rooting habit.*—Freely branching; moderately dense.

Plant description:

*Plant form/habit.*—Mounded plant habit; upright and outwardly spreading; moderately vigorous growth habit. Freely branching habit with numerous lateral branches; pinching enhances branching potential.

*Plant height.*—About 34.4 cm.

*Plant width (spread).*—About 40.4 cm.

*Lateral branches.*—Length: About 26.6 cm. Diameter: About 2 mm. Internode length: About 5 mm. Strength: Strong. Texture: Smooth, glabrous. Color, young stems: Close to 191A. Color, mature stems: Close to N187B.

Foliage description:

*Arrangement.*—Alternate, simple; sessile.

*Length.*—About 1.5 cm.

*Width.*—About 2.7 mm.

*Shape.*—Lanceolate.

*Apex.*—Acute.

*Base.*—Attenuate.

*Margin.*—Entire.

*Texture, upper and lower surfaces.*—Pubescent.

*Venation pattern.*—Pinnate.

*Color.*—Developing and fully developed leaves, upper surface: Close to 137C; venation, close to 137C. Developing and fully developed leaves, lower surface: Close to 144A; venation, close to 144A.

Flower description:

*Flower type/habit.*—Single salverform flowers; flowers face mostly upright. Freely flowering habit with about 23 flowers developing per plant. Early flowering habit, plants begin flowering about four to five weeks after planting rooted young plants.

*Fragrance.*—None detected.

*Natural flowering season.*—Long and continuous flowering habit from spring to late autumn in Higashiomi, Shiga, Japan.

*Postproduction longevity.*—Flowers last about five days on the plant; flowers not persistent.

*Flower buds.*—Height: About 1.4 cm. Diameter: About 5.9 mm. Shape: Clavate. Color: Close to 91B.

*Flower diameter.*—About 3.6 cm.

*Flower depth.*—About 1.5 cm.

*Petals.*—Quantity per flower: Typically five in a single whorl; petals fused. Length: About 2.1 cm. Lobe width: About 1.5 cm. Tube length: About 1.2 cm. Tube diameter: About 1.2 mm. Shape: Roughly spatulate. Apex: Obtuse to rounded. Margin: Slightly crenate to entire; slightly undulate. Texture, upper and lower surfaces: Smooth, glabrous. Texture, tube: Pubescent. Color: Developing petals, upper surface: Close to 85B; towards the center and venation, close to 90C; yellow eye, close to 5A. Developing petals, lower surface: Close to 85B; longitudinal lines, close to 90B. Fully expanded petals, upper surface: Close to 85B; towards the center and venation, close to 90C; yellow eye, close to 5A. With development, color becoming closer to N155A; towards the center and venation, close to 90D; yellow eye, close to 5A. Throat: Close to 154D. Tube: Close to 154D.

*Sepals.*—Quantity per flower: Typically five in a single whorl, fused at base; star-shaped calyx. Length: About 3.5 mm. Width: About 2.3 mm. Shape: Lanceolate. Apex: Acute. Margin: Entire. Texture, upper and lower surfaces: Smooth, glabrous. Color, immature, upper and lower surfaces: Towards the apex, close to 144B; towards the base, close to 145D; venation, close to N199B. Color, mature, upper and lower surfaces: Towards the apex, close to 137B; towards the base, close to 145D; venation, close to N199B.

*Peduncles.*—Length: About 1.8 cm. Diameter: About 0.9 mm. Texture: Smooth, glabrous. Color: Close to N199A.

*Reproductive organs.*—Stamens: Quantity per flower: Typically five. Stamen length: About 5.6 mm. Anther shape: Globose. Anther size: About 2.4 mm by 1.4 mm. Anther color: Close to 5D. Pollen amount: Moderate. Pollen color: Close to 7A. Pistils: Quantity per flower: One. Pistil length: About 1.5 cm. Stigma shape: Globose. Stigma color: Close to 145A. Style color: Close to 145B. Ovary color: Close to 143C. Seed/fruit: Seed and fruit development have not been observed.

Disease/pest resistance: Plants of the new *Nierembergia* have not been noted to be resistant to pathogens and pests common to *Nierembergia*.

Garden performance: Plants of the new *Nierembergia* have been observed to have good garden performance and tolerate rain, wind and temperatures from about −5° C. to about 35° C.

It is claimed:

1. A new and distinct *Nierembergia* plant named 'Intasunnipabu' as illustrated and described.

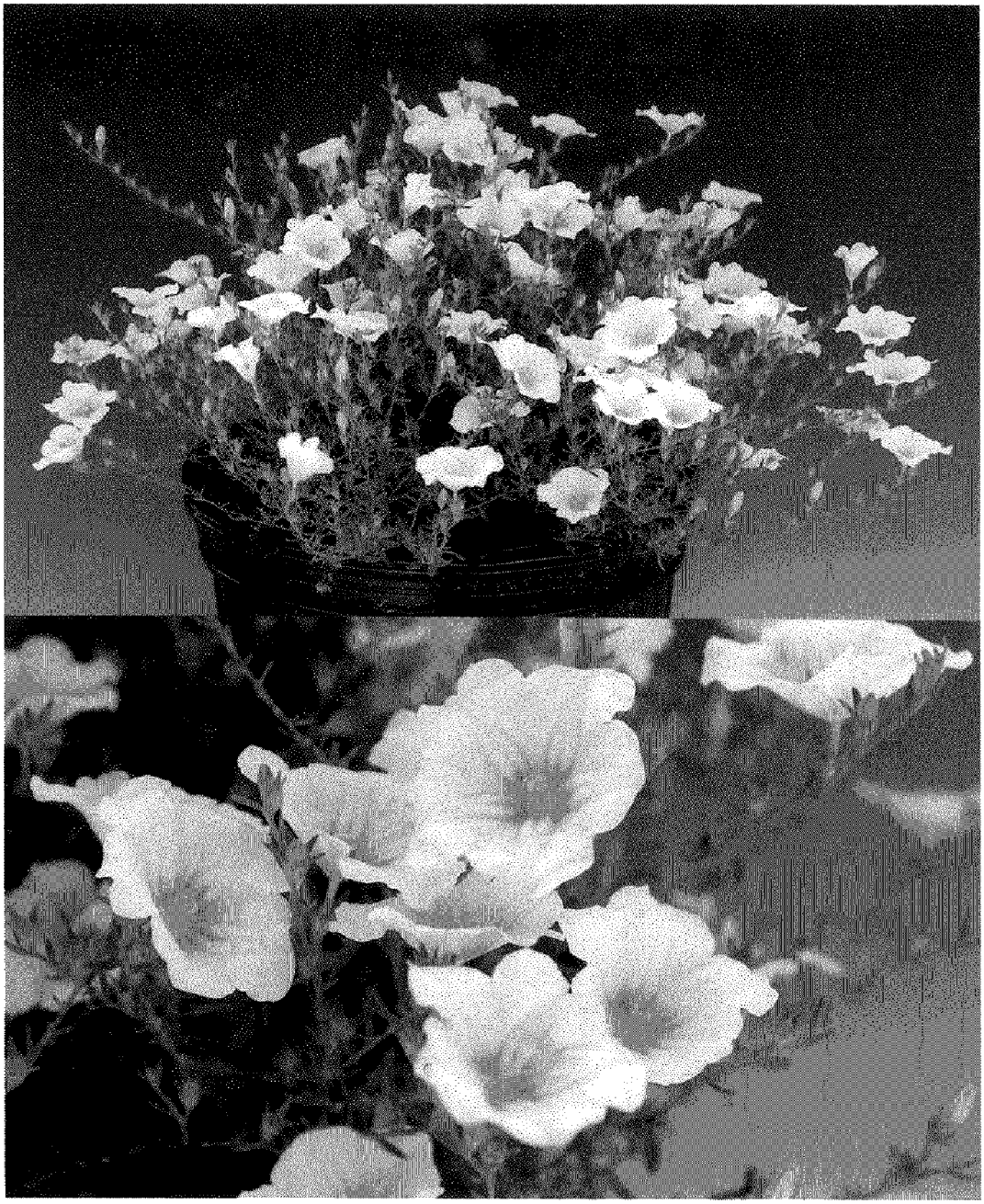

* * * * *